US008196902B1

(12) United States Patent
Pystin

(10) Patent No.: US 8,196,902 B1

(45) Date of Patent: Jun. 12, 2012

(54) METHODS AND APPARATUSES FOR PROVIDING MULTIPLE AIR FRAGRANCES

(75) Inventor: Vladimir Pystin, Sunnyvale, CA (US)

(73) Assignee: Vladimir Pystin, Sunnyvale, CA (US)

( * ) Notice: Subject to any disclaimer, the term of this patent is extended or adjusted under 35 U.S.C. 154(b) by 565 days.

(21) Appl. No.: 12/365,864

(22) Filed: Feb. 4, 2009

Related U.S. Application Data

(60) Provisional application No. 61/007,547, filed on Jun. 9, 2008.

(51) Int. Cl.
*B01F 3/04* (2006.01)

(52) U.S. Cl. ................. 261/26; 261/64.5; 261/DIG. 88; 422/4; 422/124

(58) Field of Classification Search .................... 261/30, 261/44.1, 53, 62, DIG. 88, DIG. 99, 64.5, 261/68, 70, DIG. 89; 422/4, 124, 125

See application file for complete search history.

(56) References Cited

U.S. PATENT DOCUMENTS 5,023,020 A * 6/1991 Machida et al. ............. 261/18.1
5,171,485 A * 12/1992 Ryan ............................... 261/27
5,259,062 A * 11/1993 Pelonis ......................... 392/365
5,565,148 A * 10/1996 Pendergrass, Jr. .............. 261/30
6,234,455 B1 * 5/2001 Wittek ............................ 261/30
6,524,537 B1 * 2/2003 Lee ............................... 422/124
6,581,915 B2 * 6/2003 Bartsch et al. .................. 261/26
6,712,287 B1 * 3/2004 Le Pesant et al. ............... 239/67
7,320,459 B2 * 1/2008 Johns ............................ 261/142
7,632,399 B2 * 12/2009 Geppert et al. ............... 210/127
7,722,016 B2 * 5/2010 Bradley et al. .................. 261/70
7,942,388 B2 * 5/2011 Suissa et al. .................... 261/30
7,955,552 B1 * 6/2011 Smalldon .......................... 422/5
2002/0153622 A1 * 10/2002 Hugon .......................... 261/104
2002/0158351 A1 * 10/2002 Wohrle ......................... 261/142
2006/0113687 A1 * 6/2006 Castellano ...................... 261/26

* cited by examiner

*Primary Examiner* — Charles Bushey

(74) *Attorney, Agent, or Firm* — Lowenstein Sandler PC

(57) ABSTRACT

Described herein are methods and apparatuses for providing multiple air fragrances. In one embodiment, a multi-air fragrance system for use in a vehicle includes an air fragrance block having a plurality of cartridges for storing a plurality of fragrances and a control unit that is coupled to the air fragrance block. The control unit controls a selection of one fragrance to be distributed within an interior of the vehicle. The control unit also controls an intensity of the selected fragrance to be distributed within the interior of the vehicle. In another embodiment, a portable multi-air fragrance system provides multiple air fragrances. A control unit controls a selection and intensity of a fragrance to be distributed by the portable system.

20 Claims, 16 Drawing Sheets

492 494 496 498 IN OUT 498 420 430 494 410 460 470 480 440 450 452 490 496

METHODS AND APPARATUSES FOR PROVIDING MULTIPLE AIR FRAGRANCES

RELATED APPLICATIONS

This application claims the priority benefit of U.S. Provisional Patent Application No. 61/007,547, filed on Jun. 9, 2008 and entitled, "MULTI-AIR FRAGRANCE IN THE CAR", which is incorporated herein by reference.

TECHNICAL FIELD

Embodiments of the present invention relate to providing multiple air fragrances.

BACKGROUND

In general, air fresheners provide a single air fragrance for various locations such as a home or a vehicle. For vehicles, an air freshener typically hangs from a rear view mirror thus obstructing the vision of a driver. Also, the intensity of the air fragrance is not adjustable.

Air fragrance machines typically provide a single air fragrance for a certain time period. However, the intensity of air fragrance provided sharply decreases with time. A user may find the monotony of an air fragrance bothersome. It is desirable to provide a more user friendly and desirable air fragrance machine.

SUMMARY

Described herein are methods and apparatuses for providing multiple air fragrances. In one embodiment, a multi-air fragrance system for use in a vehicle includes an air fragrance block having a plurality of cartridges for storing a plurality of fragrances and a control unit that is coupled to the air fragrance block. The control unit controls a selection of one fragrance to be distributed within an interior of the vehicle. The control unit also controls an intensity of the selected fragrance to be distributed within the interior of the vehicle.

In another embodiment, a portable multi-air fragrance system is provided to control a selection and intensity of one or more fragrances to be distributed by the portable system.

BRIEF DESCRIPTION OF THE DRAWINGS

Embodiments of the present invention are illustrated by way of example, and not by way of limitation, in the figures of the accompanying drawings and in which.

DETAILED DESCRIPTION

Described herein are methods and apparatuses for providing multiple air fragrances. In one embodiment, a multi-air fragrance system for use in a vehicle includes an air fragrance block having a plurality of cartridges for storing a plurality of fragrances and a control unit that is coupled to the air fragrance block. The control unit controls a selection of one fragrance to be distributed within an interior of the vehicle. The control unit also controls an intensity of the selected fragrance to be distributed within the interior of the vehicle.

In another embodiment, a portable multi-air fragrance system is provided to control a selection and intensity of one or more fragrances to be distributed by the portable system.

A multi-air fragrance system provides numerous advantages in comparison to prior approaches. A choice of an air fragrance and its saturation depends only on a desire of a user and does not depend on external conditions (e.g., ambient temperature in a vehicle). A user can easily select an intensity of a smell from hardly perceptible up to saturated. The plurality of cartridges provides a large quantity and various types of fragrances. An ease of installation of a cartridge enables a user of the system to create a collection of favorite smells. A cartridge can be made empty without an air fragrance such that a user can provide the air fragrance. Various types of fragrances can be distributed with the multi-air fragrance system including fragrances having medical purposes (e.g., medically essential oil, anti-allergy structures, structures for prevention of asthma, etc.), relaxing purposes (e.g., ocean smell), comically purposes, and pleasurable purposes (e.g., a smell of beer, sausage, etc.).

Figure 1:
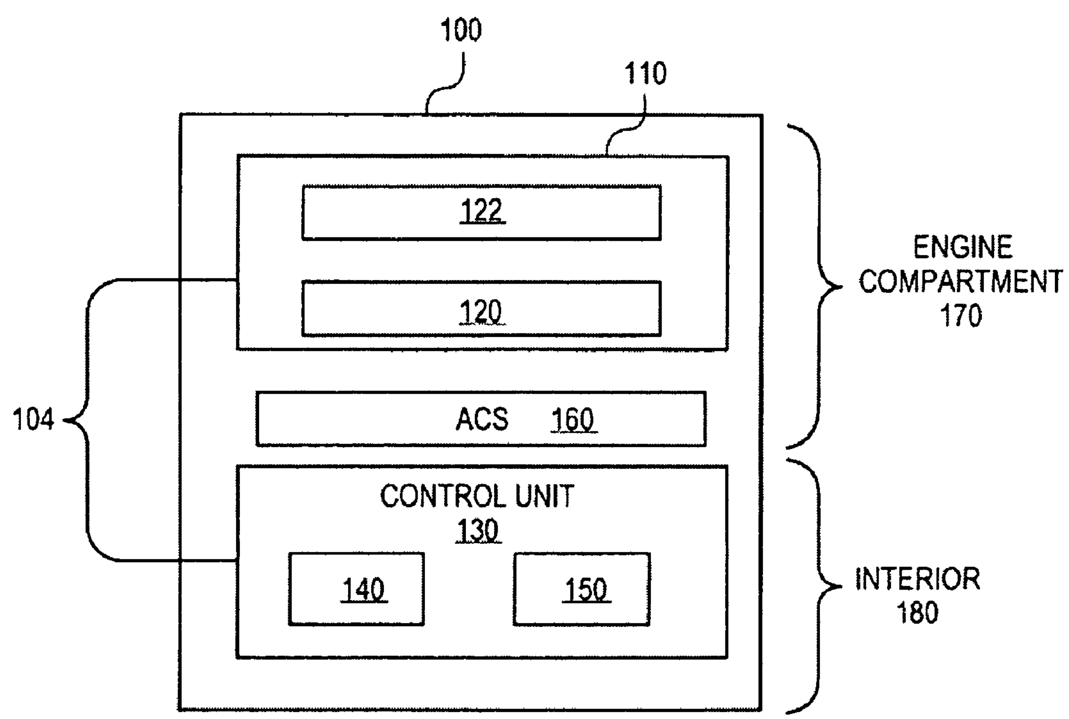
FIG. 1 illustrates a block diagram of a vehicle having an air fragrance system coupled to an air circulating system of the vehicle in accordance with one embodiment.

FIG. 1 illustrates a block diagram of a vehicle having an air fragrance system coupled to an air circulating system in accordance with one embodiment. The vehicle 100 includes an engine compartment 170 and an interior 180. The air fragrance system 104 includes an air fragrance block 110 having a plurality of cartridges 120 for storing a plurality of fragrances and a control unit 130 that is coupled to the air fragrance block 110. The control unit 130 controls a selection of one fragrance to be distributed within the interior 180 of the vehicle 100. The control unit 130 also controls an intensity of the selected fragrance to be distributed within the interior of the vehicle. The control unit 130 also includes a user interface for controlling the selection and the intensity of the fragrance to be distributed within the interior of the vehicle.

In one embodiment, a single fragrance and intensity is selected. The intensity can be changed for this fragrance by a user or the user may select a different fragrance. The one or more fragrances are distributed from the air fragrance block 110 to the interior 180 of the vehicle 100 via an air circulating system 160 of the vehicle 100.

In certain embodiments, the air fragrance block 110 includes an isolation mechanism 122 to isolate one or more fragrances which are not selected. The isolation mechanism 122 prevents these one or more fragrances from evaporating when not being selected by the control unit. Thus, the isolation mechanism prolongs service life for the air fragrances.

The isolation mechanism 122 may be integrated with or separated from the cartridges 120. The air fragrance block 110 may be located in the engine compartment 170 of the vehicle 100. Thus, no superfluous accessories (e.g. air freshener hanging from a rear view mirror) are necessary inside of a vehicle in order to obtain a variety of air fragrances.

Figure 2A:
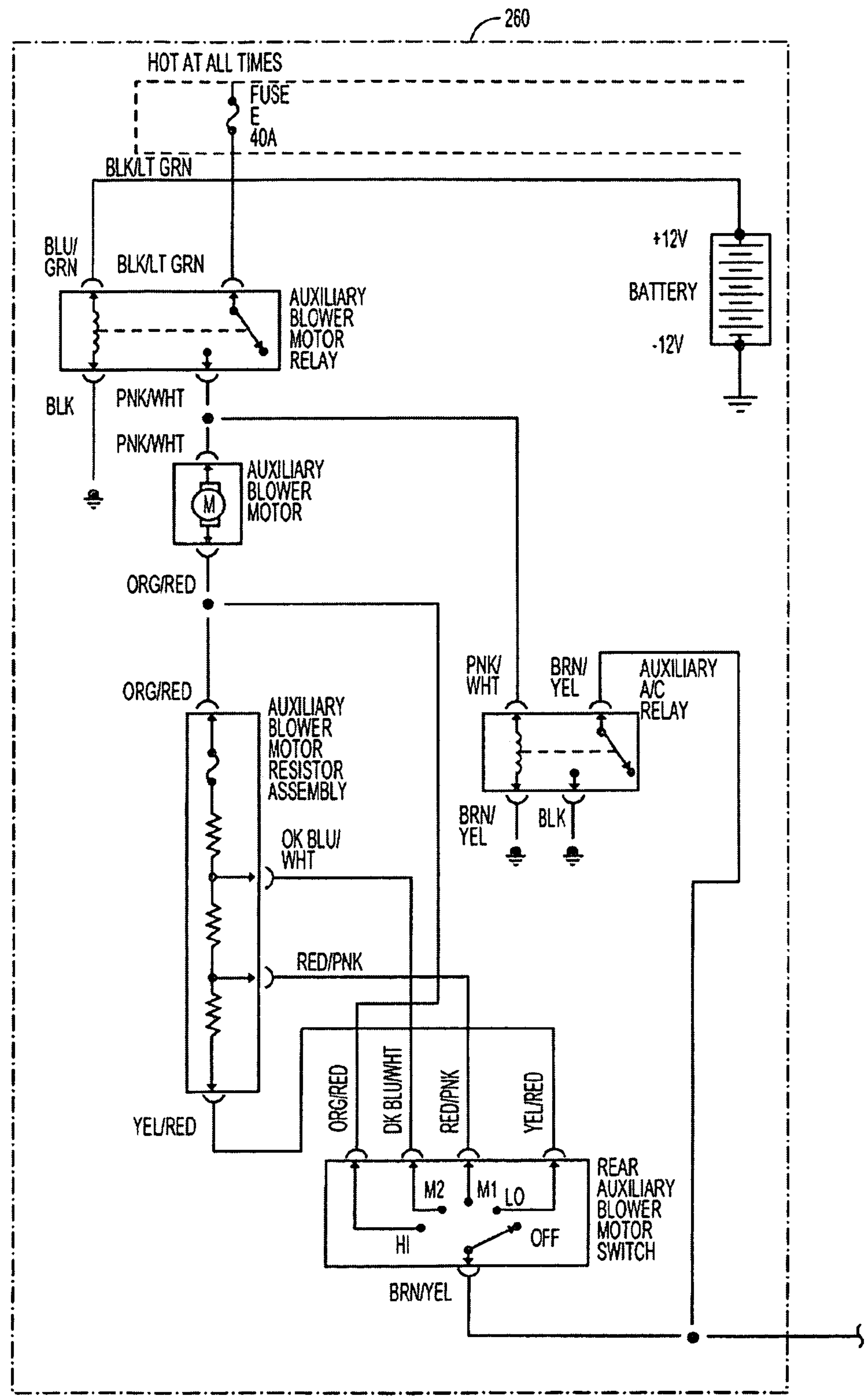
FIGS. 2A and 2B illustrate an electrical schematic diagram of an air fragrance system coupled to an air circulating system in accordance with one embodiment.
Figure 2B:
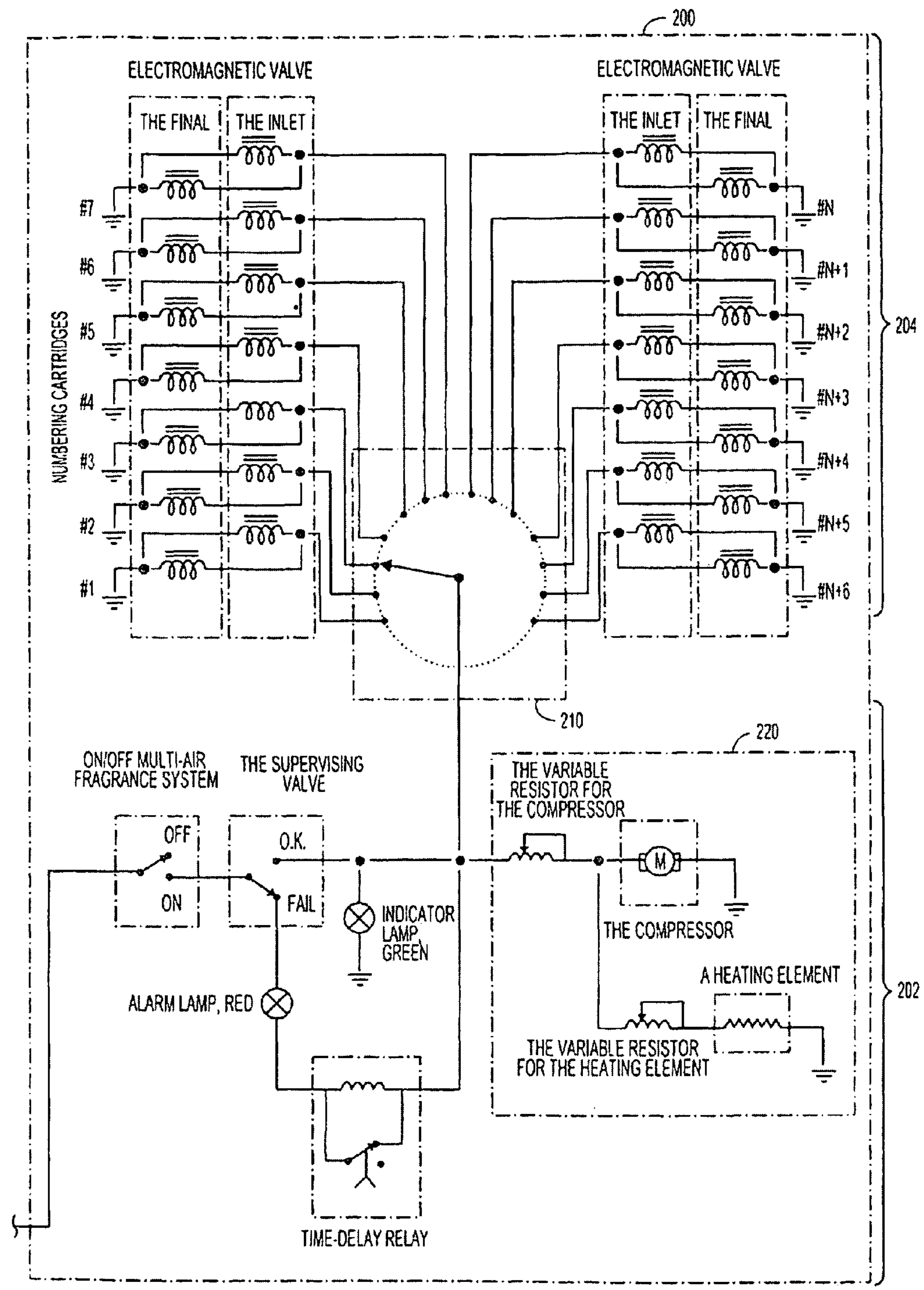

FIGS. 2A and 2B illustrate an electrical schematic diagram of an air fragrance system coupled to an air circulating system in accordance with one embodiment. The air fragrance system 200 includes a control unit 202 that is coupled to an air fragrance block 204. The control unit 202 includes an ON/OFF switch, a red alarm light, a green indicator light, a time-delay relay (e.g. 2 minutes), a selector unit 210 that is used to select a fragrance, and a selector unit 220 that controls the selection of an intensity of a selected fragrance. The air fragrance block 204 includes a supervising valve, a plurality of cartridges having the fragrances, and a plurality of electromagnetic valves.

The selector unit 210 is used to select a fragrance by opening one or more valves associated with a selected cartridge. The selector unit 220 is used to select an intensity of the selected fragrance by adjusting a variable resistor associated with a compressor and also by adjusting a variable resistor associated with a heating element. The air circulating system 260 distributes the selected fragrance to an interior of a vehicle.

Figure 3:
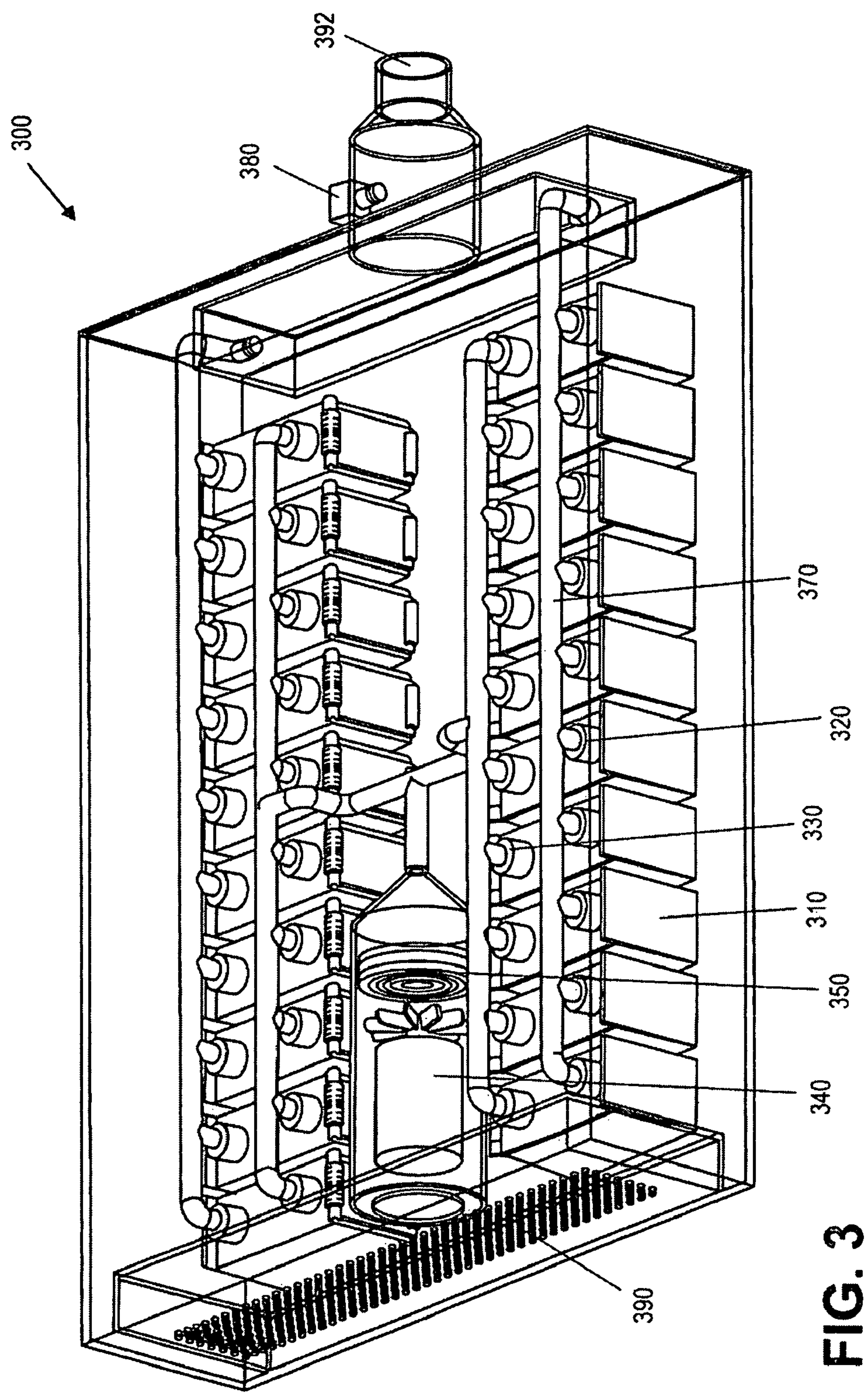
FIG. 3 illustrates an air fragrance block coupled to an air circulating system in accordance with one embodiment.

FIG. 3 illustrates an air fragrance block coupled to an air circulating system in accordance with one embodiment. The air fragrance block 300 includes cartridge cells and cartridges 310 that contain a smell of the fragrance, a final electromagnetic valve 320 associated with each cartridge 310, an inlet electromagnetic valve 330 associated with each cartridge 310, a compressor 340, a heating element 350, an inlet air line 360, a final air line 370, a supervising valve 380, and an air intake 390. The air fragrance block 300 is coupled to an air circulating system 392 that may include ventilation, air conditioning, and heating.

Cartridge cells are inserted into cartridges, which will be described in conjunction with FIG. 6. The final electromagnetic valves 320 provide a release of an air mix enriched with a fragrance in a final air line 370. The valves also provide a hermetic sealing of a cartridge in a non-working condition and prevent evaporation of its contents.

Inlet electromagnetic valves 330 are placed at an entrance to cells of cartridges. In operation, the chosen electromagnetic valve opens and passes an air stream in a cartridge where the air stream is enriched with a fragrance and leaves through the final electromagnetic valve in a final air line 370. A switched off condition protects a cartridge from drying out.

The compressor 340 creates air pressure in the air fragrance system. The heating element 350 heats an air stream, which is created by the compressor, and is intended for cartridges with jelly-like liquid or solid substances having a smell contained within the cartridges. The inlet air line 360 transfer an air stream from the compressor to a cell of a cartridge. The final air line 360 provides a transfer of the air mix enriched with a smell from a cell of a cartridge to the air circulating system 392. The supervising valve 380 provides an indication of serviceability of the chosen cartridge with two conditions:

FAIL—if the system has no increased pressure, then the valve 380 disconnects the multi-air fragrance system or a faulty cartridge, PASS—if the system and the chosen cartridge are in working order.

Figure 4:
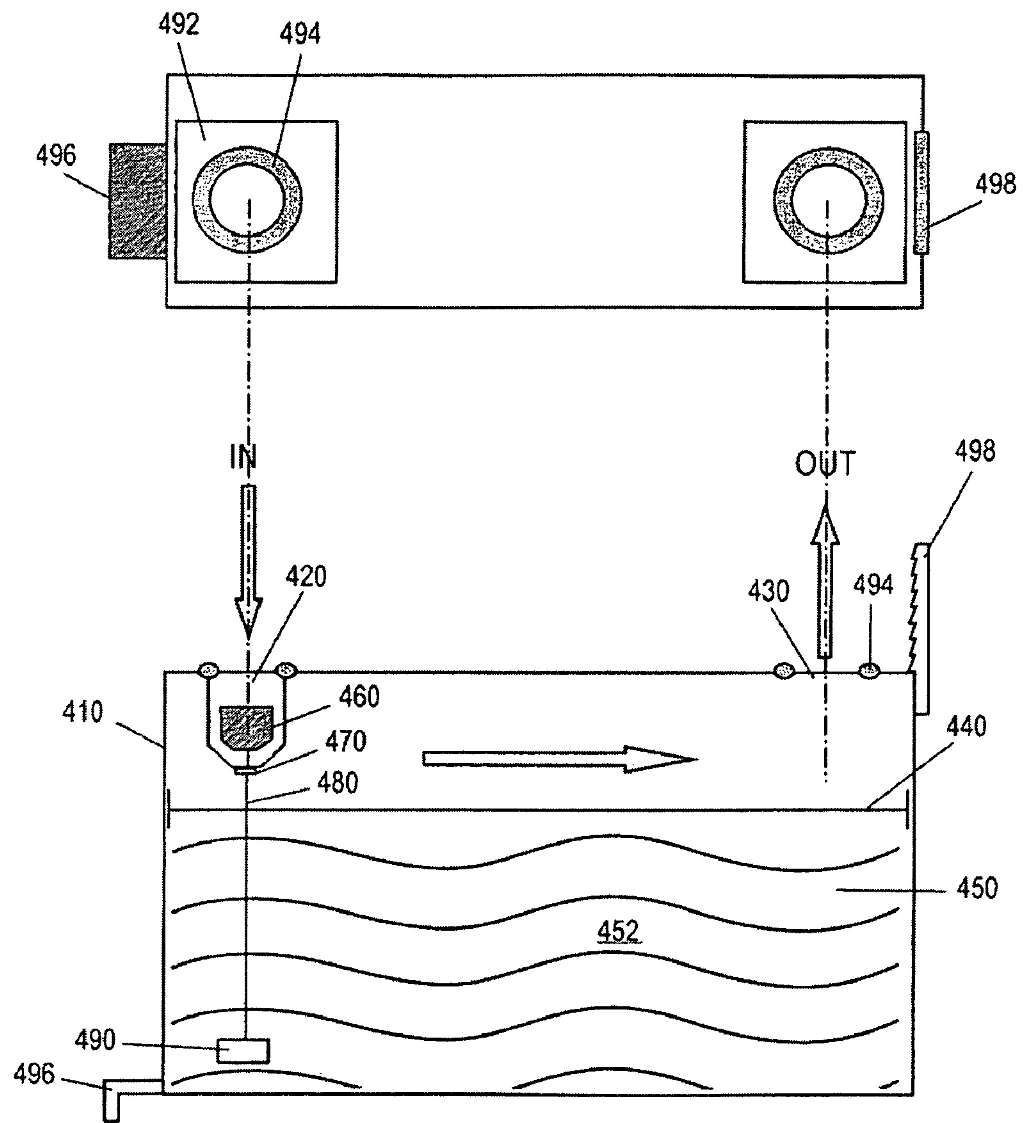
FIG. 4 illustrates a cartridge of an air fragrance block in accordance with one embodiment.

FIG. 4 illustrates a cartridge of an air fragrance block in accordance with one embodiment. The cartridge 410 includes a structure capable of having a fragrance. The cartridge 410 also includes an entrance channel 420, an exit channel 430, a smoothing grid 440 for liquid smell-containing structures, a smell-containing structure 450, a supervising valve 460, a terminator 470, a pin 480, a float 490, a protective film 492, an O-ring 494, a persistent fixture 496, and a fixing fixture 498.

The cartridge 410 represents a hermetic vessel in which is located a smell-containing structure 450 that includes a structural component for containing a fragrance in a liquid, jelly-like liquid, and/or firm form. Within the entrance channel 420 there is a control (alarm) valve which includes the supervising valve 460, height terminator 470, and the float 490. All of these components fasten on the pin 480 (e.g., plastic pin, metal pin).

The O-ring, which acts as a sealant, is located on top of the entrance channel 420 and also on top of the exit air channel 430 to provide tight connections with branch pipes of an entrance and exit air line cartridges cells.

Figure 5:
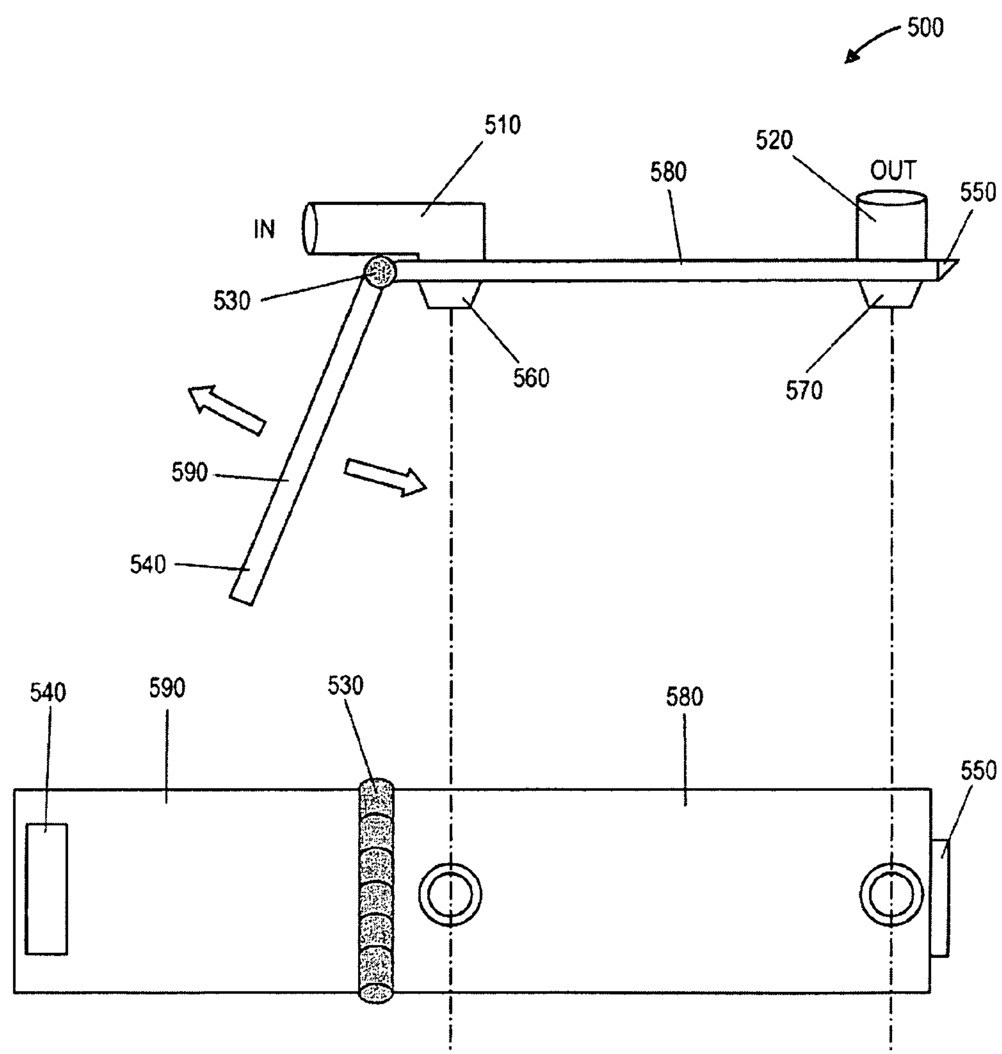
FIG. 5 illustrates a cartridge cell of an air fragrance block in accordance with one embodiment.

For transportation of new cartridges, the protective film 492 blocks outflow and also prevents evaporation of a smell. It is established at a factory manufacturer, after filling cartridges of the smell-containing structure 450. Persistent and fixing fixtures 496 and 498 are intended for fastening a cartridge to cartridge cells as illustrated in FIGS. 5 and 6. For this purpose in cartridge cells, a window 540 of FIG. 5 is aligned with a persistent fixture 496 and a tooth 550 is coupled to the fixing fixture 498 of a cartridge. The cartridge cell 500 also includes an inlet air line 510, a final air line 520, a hinge strap 530, a branch pipe 560 of the inlet air line 510, a branch pipe 570 of a final air line 520, a base 580 of the cartridge cell, and a mobile wall 590 of the cartridge cell.

Figure 6:
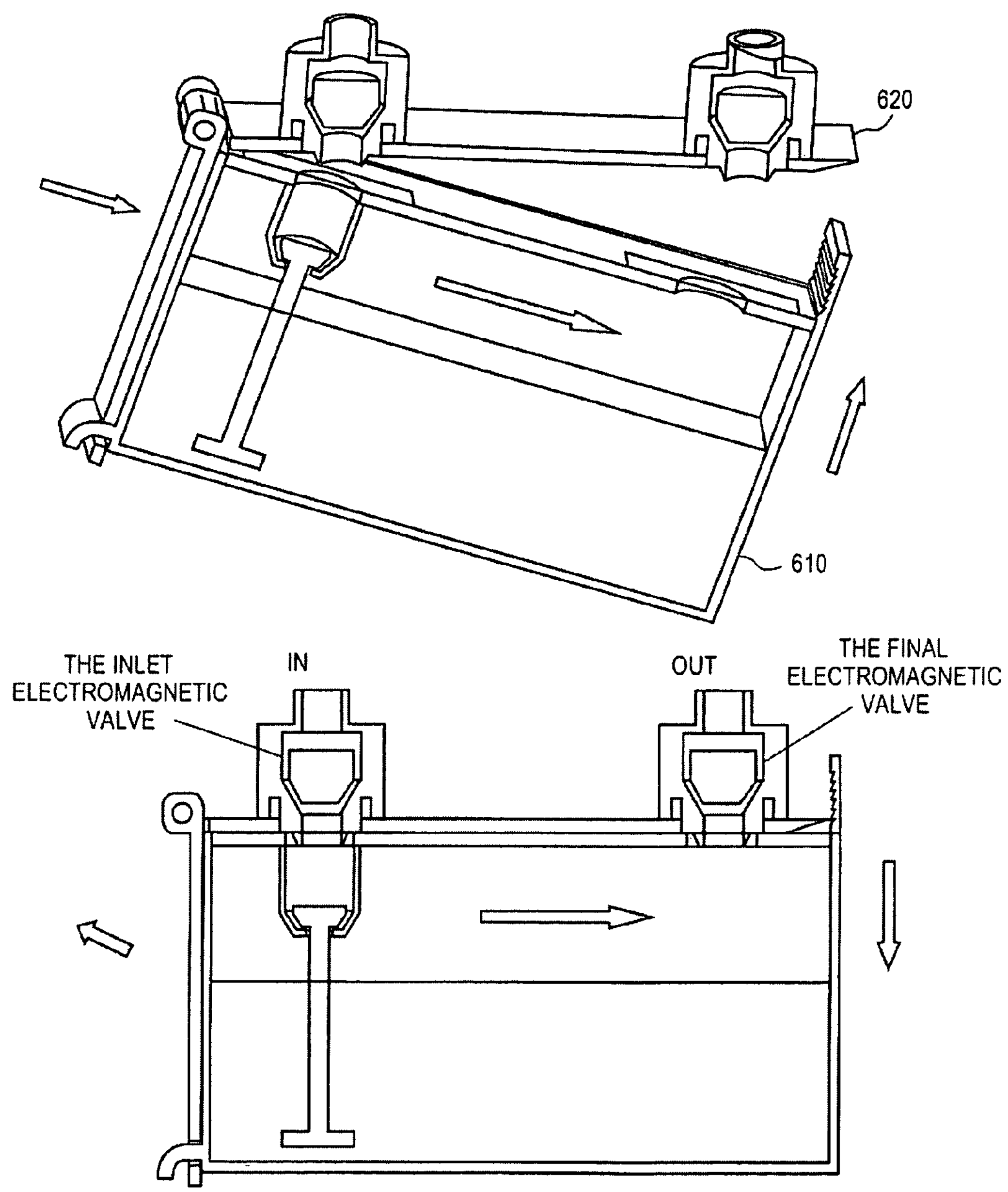
FIG. 6 illustrates fastening of a cartridge cell with a cartridge in accordance with one embodiment.

FIG. 6 illustrates the fastening of the cartridge cell to the cartridge in accordance with one embodiment. The entrance channel 420 of the cartridge 410 is aligned with the inlet air line 510 of the cartridge cell 500. The exit channel 430 of the cartridge 410 is aligned with the final air line 520 of the cartridge cell 500. A window 540 is aligned with the persistent fixture 496 and the tooth 550 is coupled to the fixing fixture 498 of the cartridge 410.

In one embodiment, a supervising valve 460 of the cartridge 410 operates as follows. Before the smell-containing structure 450 that generates the fragrance has evaporated, and was lowered below a float, on it pushes out force which holds the supervising valve 460 open in a normal operating condition. As the smell-containing structure 450 evaporates, it passes a minimal level, the float 490 lowers, the supervising valve 460 lowers together with a float, and blocks access of submission of air in a cartridge.

The supervising valve 460 in a closed position prevents a user from being able to select this cartridge and select an intensity for the fragrance in the cartridge. In this case, the air fragrance system generates an alarm signal (e.g., red light in FIG. 2) that indicates a non-working cartridge potentially having no more fragrance, and if a user does not select a different working cartridge, the multi-air fragrance system turns off. The supervising valve 460 prevents a fragrance from evaporating from the cartridge and indicates when the smell-containing structure will end. Thus, the air fragrance system provides a signal to a passenger inside a vehicle when the cartridge needs its replacement.

A smoothing grid 440 is established in the top part of a cartridge above a liquid level of a smell-containing structure 450. The smoothing grid prevents the liquid from moving into air channels of a cartridge, which can occur if the cartridge vibrates from various reasons including automobile vibrations.

Figure 7:
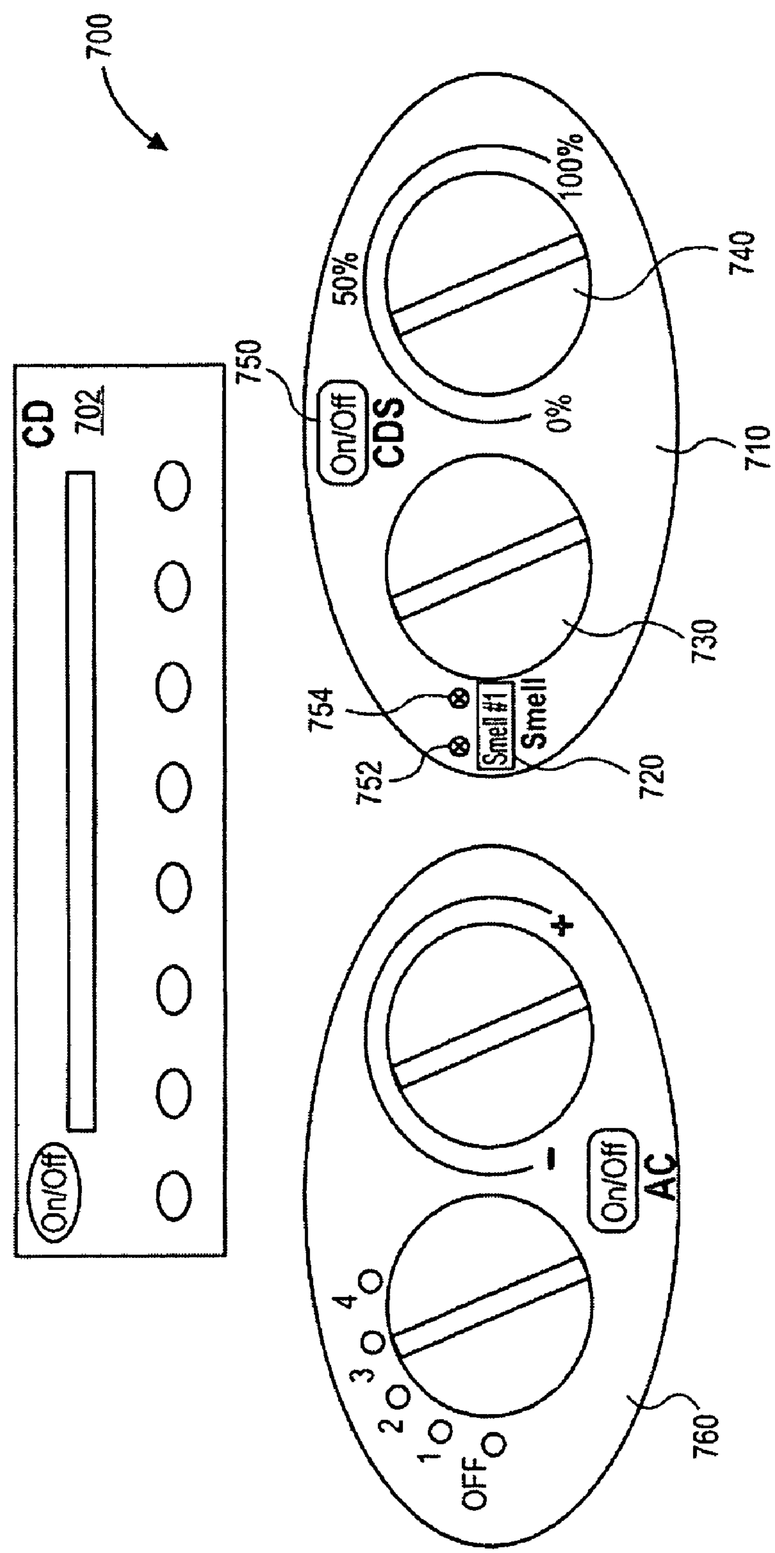
FIG. 7 illustrates a control unit in accordance with one embodiment.

FIG. 7 illustrates a user interface of a control unit in accordance with one embodiment. The user interface 700 includes a compact disc (CD) player 702, a selector unit 760 of an air circulating system, and a selector unit 710 for selecting a fragrance with a selector 730 and also for selecting an intensity of the selected fragrance with a selector 740. The selector unit 710 further includes a display 720 of a selected fragrance or smell, and an ON/OFF selector 750 for the air fragrance system. The selector unit 710 also includes alarm light 752 (e.g., red light) and indicator light 754 (e.g., green light) which indicates if a selected cartridge is in a working condition. The user interface 700 of the control unit is located inside a vehicle and may include other components as well.

Figure 8:
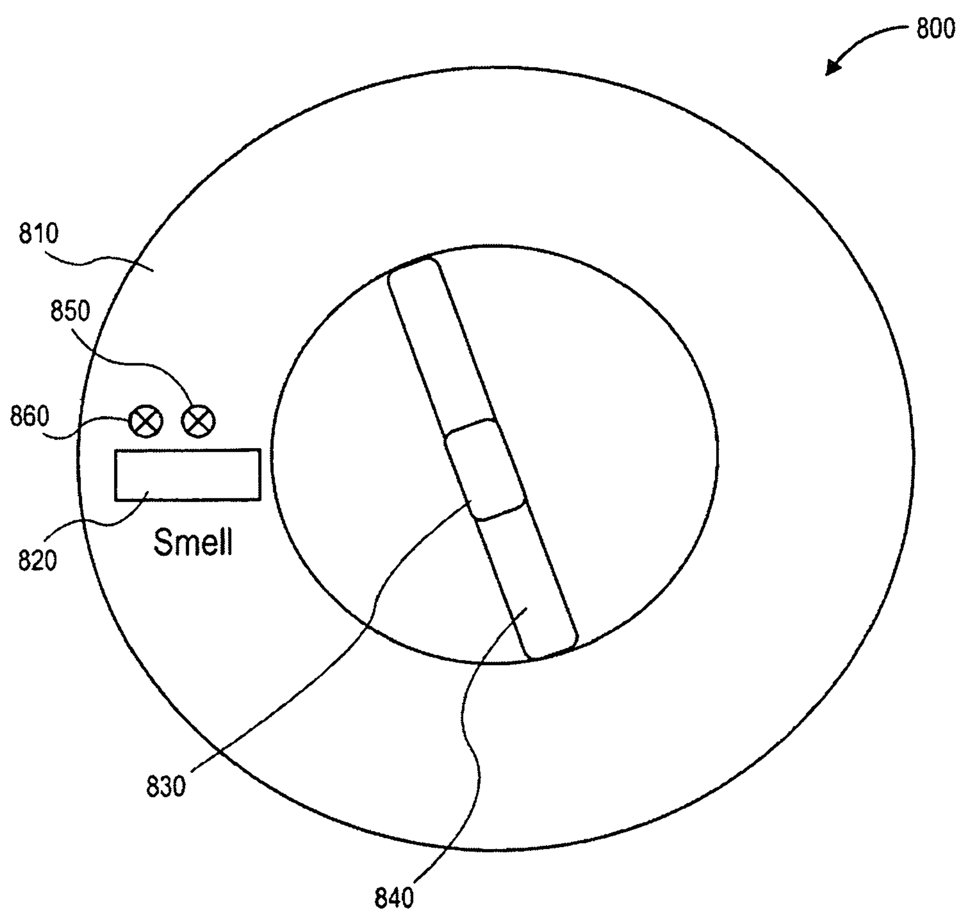
FIG. 8 illustrates a selector unit for selecting an air fragrance in accordance with one embodiment.

FIG. 8 illustrates a selector unit for selecting an air fragrance in accordance with one embodiment. The selector unit 800 is similar to the selector unit 710 described above. The selector unit 800 includes a decorative panel 810, a window 820 for display of the name of a smell, a decorative fixing bolt 830, a selector 840 (e.g., handle of management of a choice of a smell), an indicator light 850, and an alarm light 860. The window 820 may include an optional magnifying lens. In an embodiment, a green indicator light 850 indicates that a selected cartridge is operable and a red alarm light 860 indicates that the selected cartridge is inoperable in a non-working condition.

Figure 9:
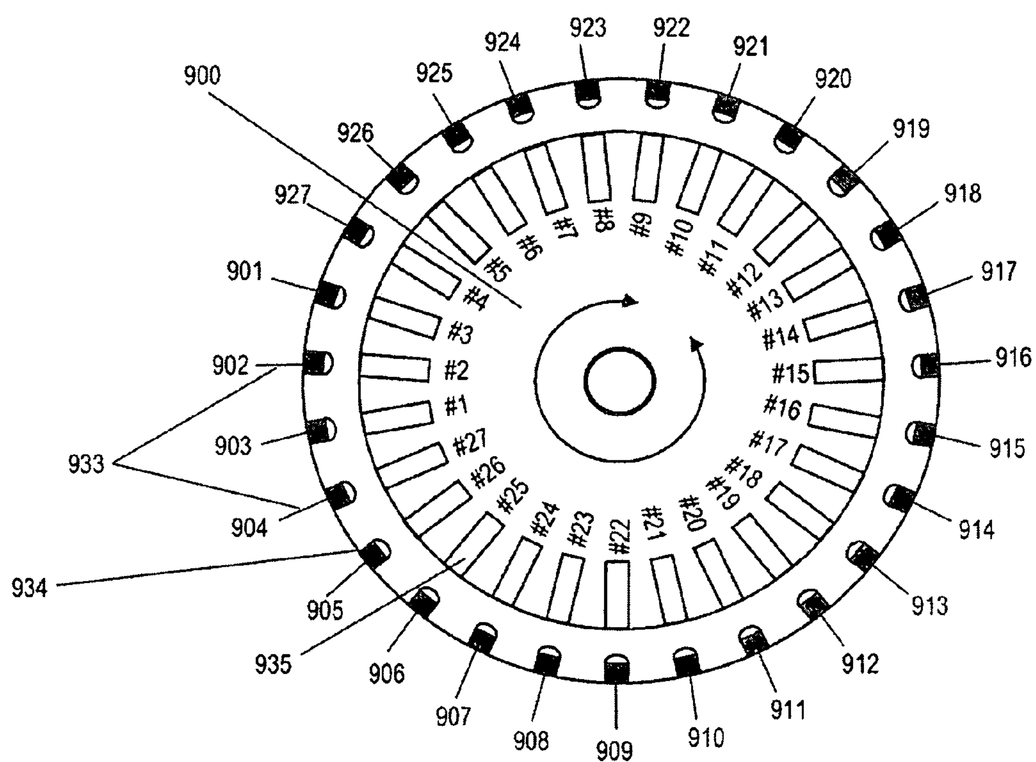
FIG. 9 illustrates a disk of management for selecting an air fragrance in accordance with one embodiment.

FIG. 9 illustrates a disk of management for selecting an air fragrance in accordance with one embodiment. A disk 900 of management of a choice or selection of a smell includes a managing contact 932 of a choice of a smell, connecting wires 933, a group of contacts 934 numbered 1-27, a place for labels of the name of a smell, and numbered cartridges (e.g., 1-27).

The disk 900 is formed of a metal or plastic disk with a managing contact 932 that is aligned with one of the contacts 1-27 in order to select a cartridge. On the disk 900, numbers of cells of cartridges are designated in a clockwise manner, and opposite to them a dotted line designates a place for a label of the name of a smell of a cartridge (the label should be provided together with a cartridge).

The group of contacts is numbered 1-27 in a counterclockwise manner, each contact connects to the inlet and final electromagnetic valves, corresponding cell of a cartridge in the air fragrance block illustrated in FIGS. 2 and 3.

A user can select a particular cartridge by aligning the managing contact 932 with one of the contacts 1-27 associated with one of the cartridges by using the selector 830. Then, an electric circuit is created with contact of the chosen cartridge in the group of contacts. The inlet and final electromagnetic valves of the chosen cell of a cartridge open access to an air stream to a cartridge.

Figure 10:
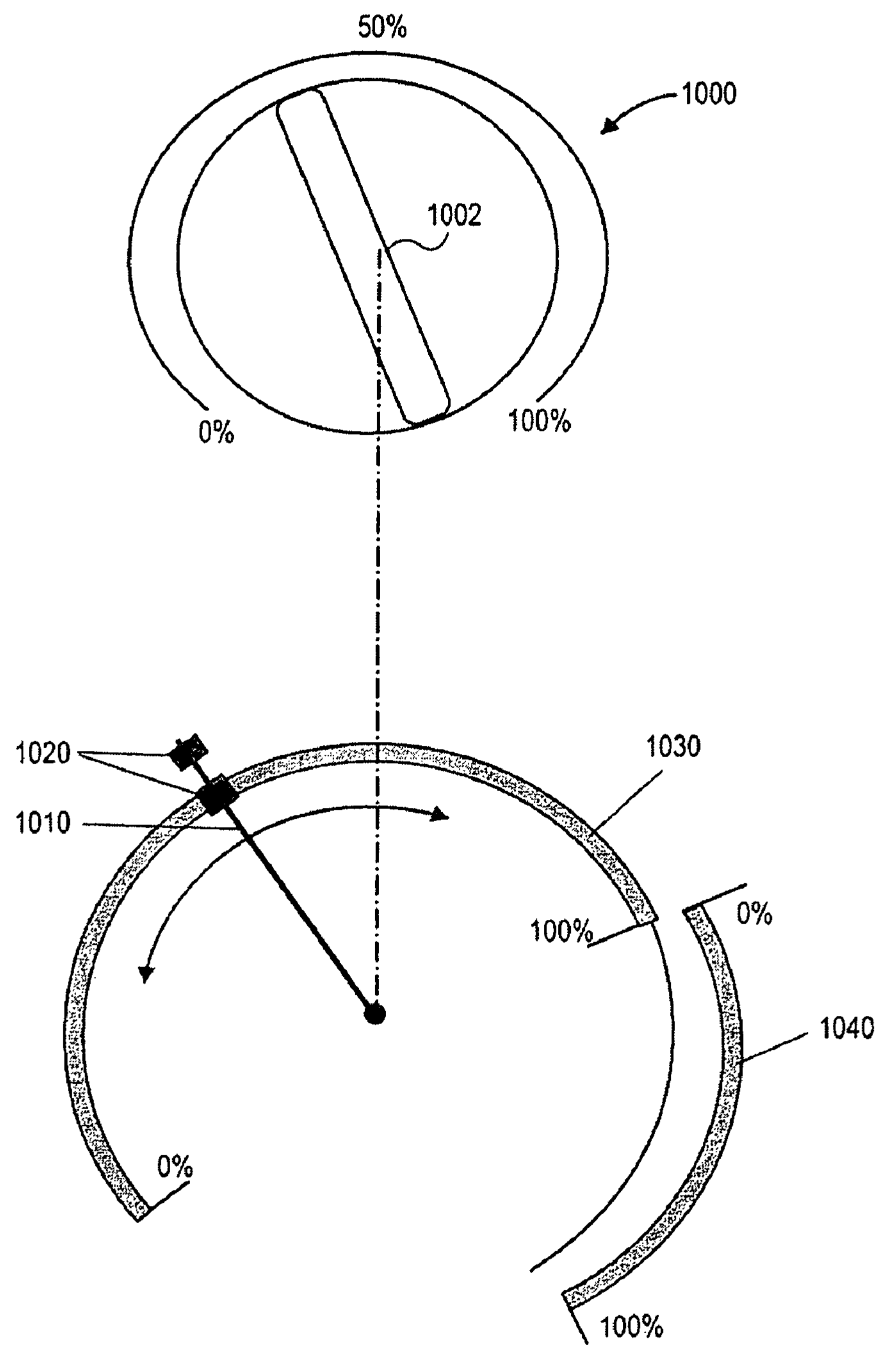
FIG. 10 illustrates a selector unit for selecting an intensity of a selected air fragrance in accordance with one embodiment.

FIG. 10 illustrates a selector unit for selecting an intensity of a selected air fragrance in accordance with one embodiment. The selector unit 1000 includes a selector 1002, which can be varied to adjust an intensity of a selected fragrance. A toddler 1010 of the group of contacts attaches to the contacts 1020. The selector unit 1000 further includes a variable resistor 1030 for a compressor, and a variable resistor 1040 for a heating element. The variable resistor 1030 is responsible for operation of the electric motor of the compressor. The variable resistor 1040 is responsible for operation of the heating element.

Moving the selector 1002 of intensity of a smell causes the toddler 1010 to move the variable resistor, which manages the compressor. Inclusion of a heating element occurs at achievement of capacity of the compressor of equal to 100% (approximately 60-70% from the general course of a regulator), further the compressor works in a 100% mode, with heat included as an element with capacity from 0 up to 100%.

Realization of management of a choice of a smell, its intensity, and displays can occur with an electronic user interface rather than the mechanical kind described above. For example, in a cartridge it is possible that the required temperature, mode, air flow mixes, etc. is provided with a microcircuit in which there can be a name of the cartridge. Display of the chosen smell can be made on an electronic board and etc.

Figure 11:
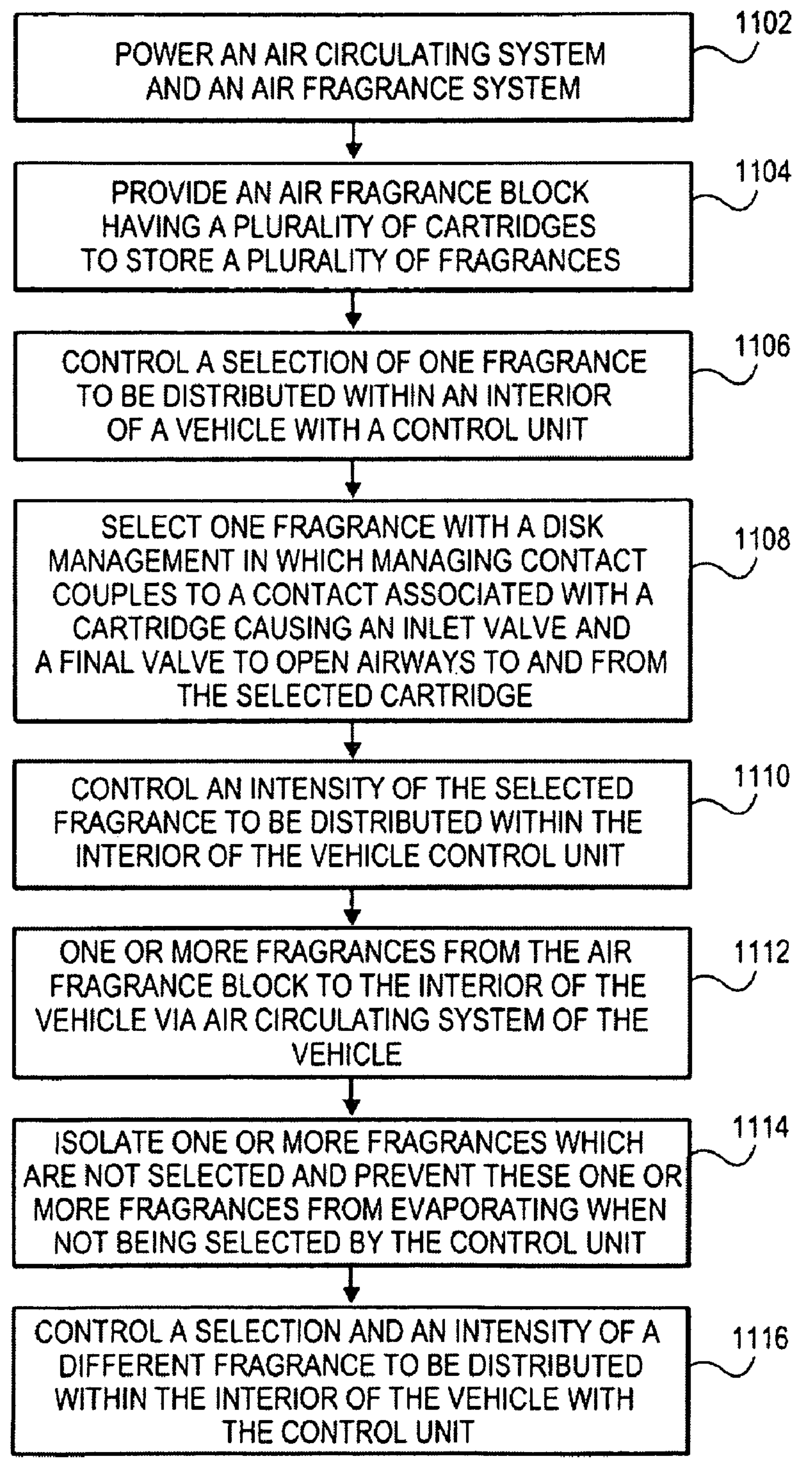
FIG. 11 illustrates one embodiment of a method for providing multiple air fragrances in accordance with one embodiment.

FIG. 11 illustrates one embodiment of a method for providing multiple air fragrances in accordance with one embodiment. The method includes powering an air circulating system and an air fragrance system at block 1102. The method further includes providing an air fragrance block having a plurality of cartridges to store a plurality of fragrances at block 1104. Next, the method includes controlling a selection of one fragrance to be distributed within an interior of a vehicle with a control unit at block 1106. Next, the method includes controlling the selection of one fragrance by selecting one fragrance with a disk of management in which a managing contact couples to a contact associated with a cartridge causing an inlet valve and a final valve to open airways to and from the selected cartridge at block 1108. Next, the method includes controlling an intensity of the selected fragrance to be distributed within the interior of the vehicle with the control unit at block 1110. Next, the method includes distributing one or more fragrances from the air fragrance block to the interior of the vehicle via the air circulating system of the vehicle at block 1112.

Next, the method includes isolating one or more fragrances which are not selected and preventing these one or more fragrances from evaporating when not being selected by the control unit at block 1114. Next, the method includes controlling a selection and an intensity of a different fragrance to be distributed within the interior of the vehicle with the control unit at block 1116.

Figure 12:
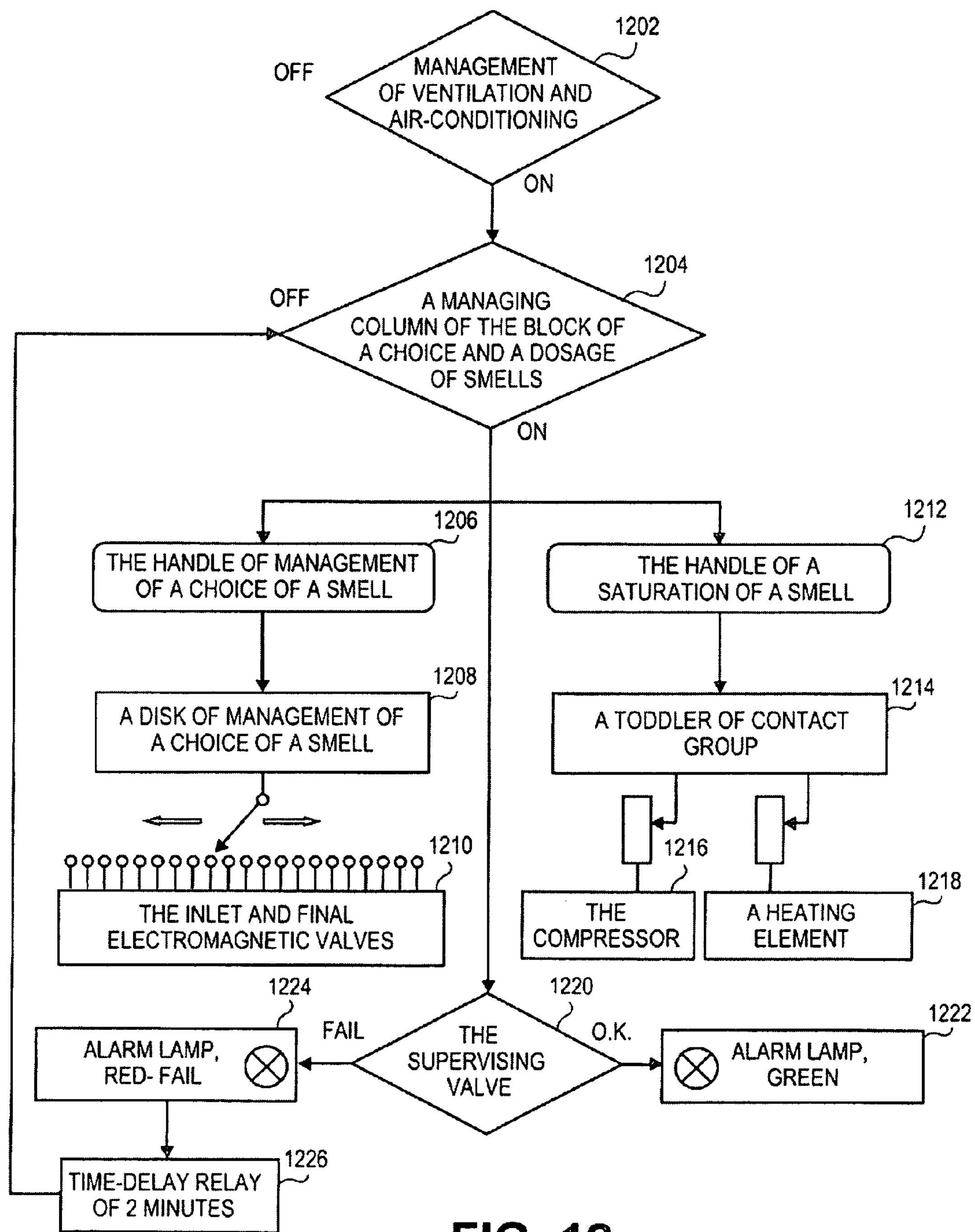
FIG. 12 illustrates another embodiment of a method for providing multiple air fragrances in accordance with another embodiment.

FIG. 12 illustrates another embodiment of a method for providing multiple air fragrances in accordance with another embodiment. A user (e.g., driver or passenger), being in an interior of the automobile, is able to obtain multiple air fragrances. The user turns ON an air circulating system (e.g., ventilation or the air condition) at block 1202 and also turns ON an air fragrance system at block 1204 by pressing an ON/OFF button for each system. Next, the user chooses on panel CDS of FIG. 7 a fragrance at block 1206. For example, the user begins to smell the selected fragrance under the name "CITRIC", by means of the selector 730 (e.g., handle of management of a choice of a smell) illustrated in FIG. 7. Next, the user determines a required intensity of submission of a smell by means of another selector 740 (e.g., the handle of a saturation of a smell) at block 1212.

An electric circuit is formed, through a disk of management of a choice of a smell illustrated in FIG. 9, on which managing contact and another contact are coupled together based on the selection of the fragrance at block 1208. This causes a pressure on the inlet and final electromagnetic valves in the air fragrance block. Upon submission of the pressure, the valve opens access to a selected smell-containing cartridge at block 1210. The management of a compressor at block 1216 and a heating element at block 1218 occurs with the help of variable resistors through a toddler of a group of contacts at block 1214, and illustrated in FIG. 10.

The compressor forces air through air intake in the air line and through the open valves of an electromagnetic relay. Air enters a cartridge and passes through a smell-containing structure. The air mix creates air pressure in a final air line, a supervising valve reacts to it at block 1220, and illuminates on panel CDS a green display bulb 754 at block 1222. Further the air mix is distributed in the interior of the automobile through the air circulating system of ventilation and air-conditioning.

If a smell-containing structure in a cartridge is absent, a float in a cartridge falls due to its weight and the supervising valve of a cartridge blocks the entrance air channel of a cartridge. Air does not pass through the cartridge and does not get in the final air line. In response to this, the supervising valve reacts at block 1220, submitting a signal to panel CDS as a red bulb 752 of the alarm system at block 1224. If change of a smell has not followed within a time period (e.g., 2 minutes) after inclusion of a red bulb of the alarm system at block 1226, the relay of the supervising valve disconnects the multi-air fragrance system.

A user can easily install a new cartridge with a smell-containing structure as follows.

1. To choose a free cartridge and remember its number in relation to other cartridges.
2. To establish a cell cartridge in the free cartridge as illustrated in FIG. 6 so that a persistent fixture of the cartridge couples to a window for persistent fixture to a mobile wall of the cartridge cell. Holding it for the bottom edge, a user makes a vertical movement. A fixing fixture of the cartridge snaps together with a tooth of the cartridge cell.
3. In an interior of the automobile, on panel CDS, a user turns a decorative fixing bolt of a handle of management of a choice of a smell. A user removes the handle and the decorative panel. On a disk of management of a choice of a smell, a user locates a place with a number of a cartridge, and pastes a label with the name of a cartridge which should be delivered together with a cartridge in a right place for a label of the name of a cartridge as illustrated in FIG. 9.
4. A user turns the bolt on the decorative panel to reattach the handle of management of a choice of a smell to the decorative panel.

To remove a cartridge from a cartridge cell it is necessary to unbend a fixing fixture of a cartridge from a basis cartridge cells illustrated in FIG. 5 and put the cartridge down and remove it from the cartridge cell.

In one embodiment, the method of FIG. 12 can be used to provide multiple fragrances within a portable air fragrance system. The operations are similar to those described above in conjunction with FIG. 12, except the method for operating the portable system has no block 1202 because the portable system operates independently and is not coupled to a ventilation and air conditioning system in a vehicle.

Figure 13:
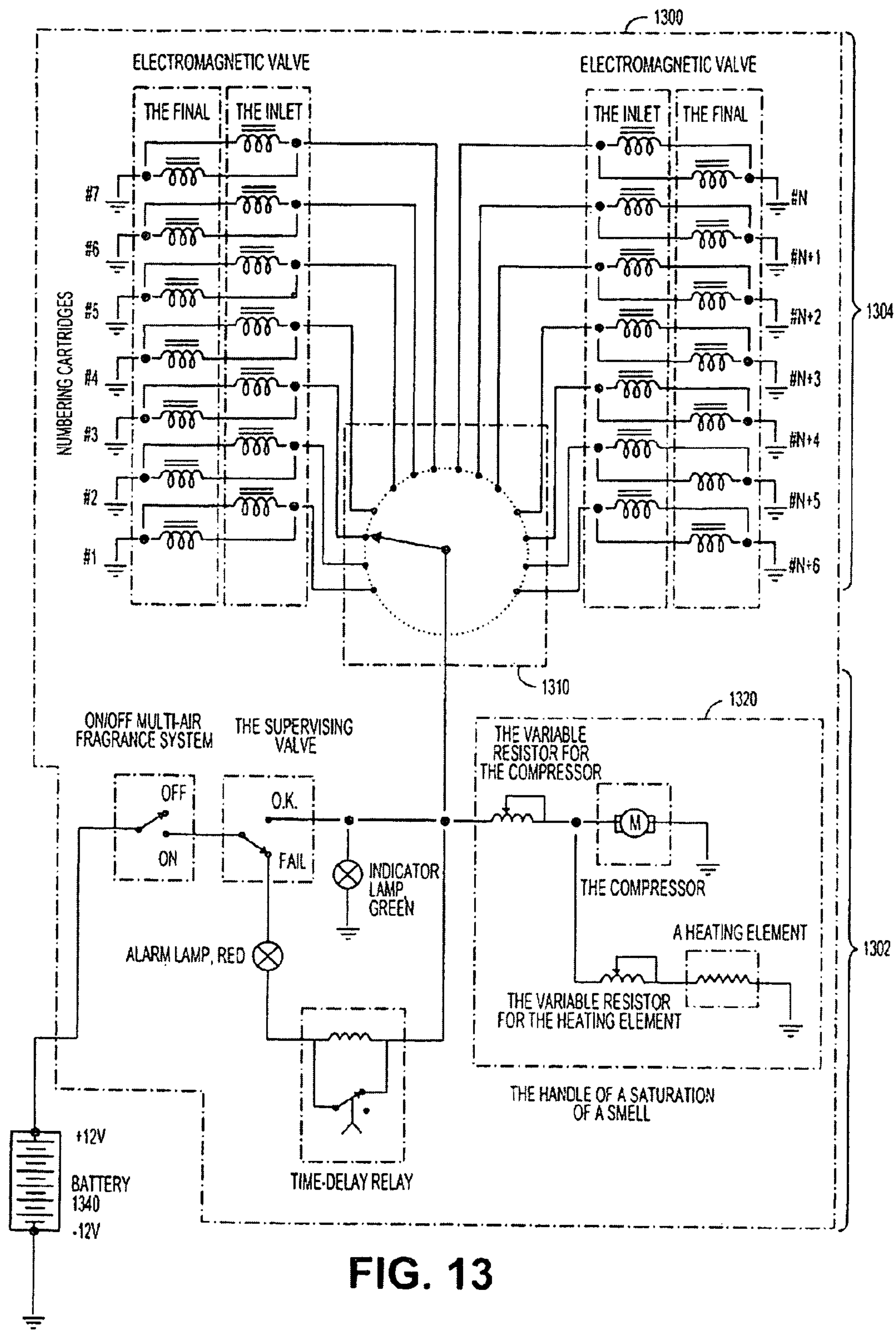
FIG. 13 illustrates an electrical schematic diagram of a portable air fragrance system in accordance with one embodiment.

FIG. 13 illustrates an electrical schematic diagram of a portable air fragrance system in accordance with one embodiment. The system 1300 includes a control unit 1302 that is coupled to an air fragrance block 1304. The control unit 1302 includes an ON/OFF switch, a red alarm light, a green indicator light, a time-delay relay (e.g., 2 minutes), a selector unit 1310 that is used to select a fragrance, and a selector unit 1320 that controls the selection of an intensity of a selected fragrance. The air fragrance block 1304 includes a supervising valve, a plurality of cartridges having the fragrances, and a plurality of electromagnetic valves.

The selector unit 1310 is used to select a fragrance by opening one or more valves associated with a selected cartridge. The selector unit 1320 is used to select an intensity of the selected fragrance by adjusting a variable resistor associated with a compressor and also by adjusting a variable resistor associated with a heating element.

The portable system 1300 includes similar components in comparison to the stationary system 200 illustrated in FIG. 2. However, portable system 1300 is not coupled to an air circulating system and is powered with its own battery 1340.

Figure 14:
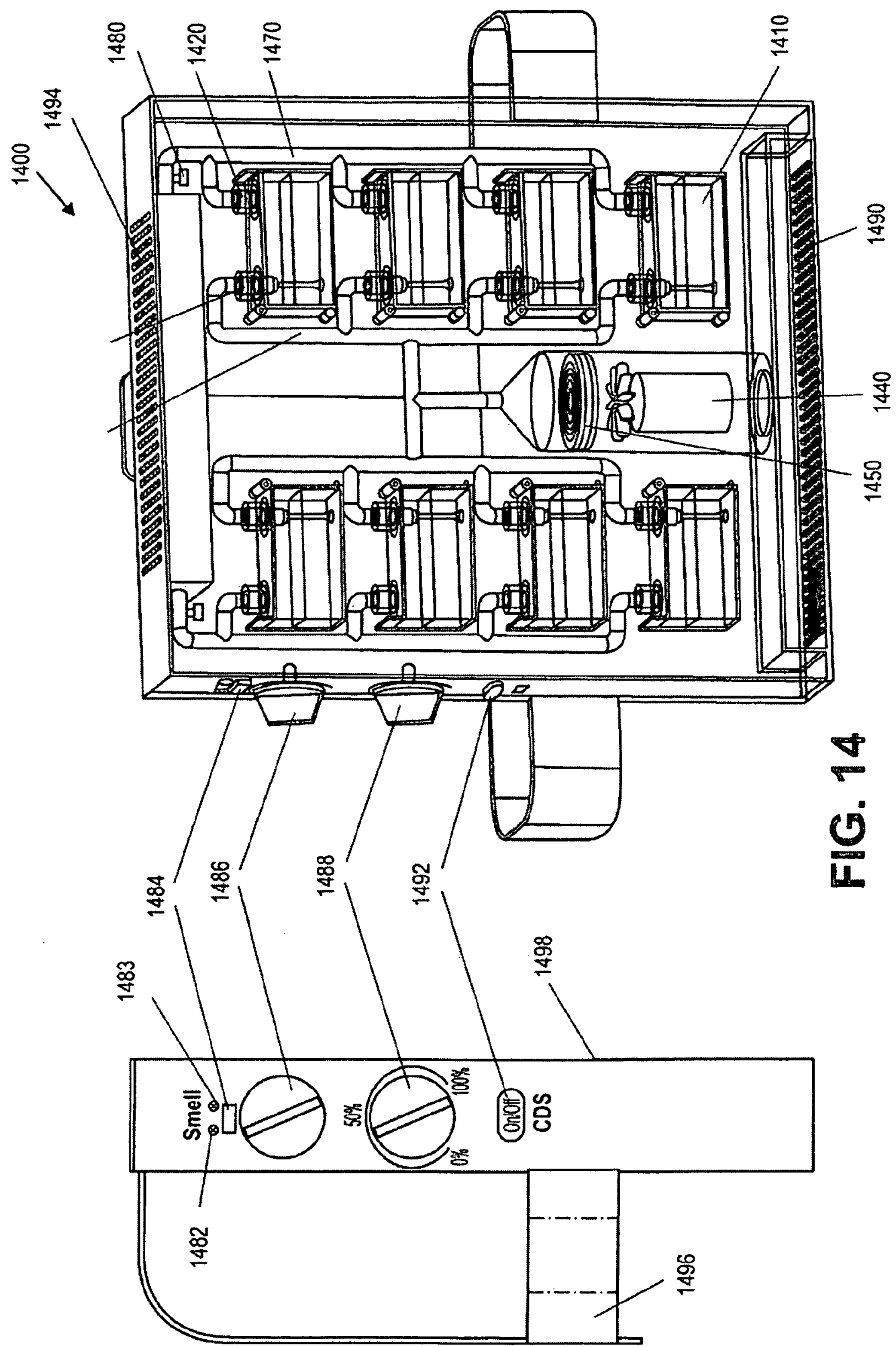
FIG. 14 illustrates an air fragrance block of a portable system in accordance with one embodiment.

FIG. 14 illustrates an air fragrance block of a portable system in accordance with one embodiment. The air fragrance block 1402 of a portable system 1400 includes cartridge cells and cartridges 1410 that contain a smell of the fragrance, a final electromagnetic valve 1420 associated with each cartridge 1410, an inlet electromagnetic valve 1430 associated with each cartridge 1410, a compressor 1440, a heating element 1450, an inlet air line 1460, a final air line 1470, a supervising valve 1480, and an air intake 1490. These components are similar to the components described in conjunction with FIG. 3 and work in a similar manner.

The portable system 1400 includes a user interface 1400 that includes a selector unit 1486 for selecting a fragrance and also a selector unit 1488 for selecting an intensity of the selected fragrance. The selector unit 1486 further includes a display 1484 of a selected fragrance or smell, and an ON/OFF selector 1492 for the air fragrance system. The selector unit 1486 also includes alarm light 1482 (e.g., red light) and indicator light 1483 (e.g., green light) which indicates if a selected cartridge is in a working condition.

The portable system 1400 also includes a fragrance diffuser 1494 and a belt 1496 which is used to attach the portable system 1400 to other objects (e.g., an automobile seat).

Figure 15:
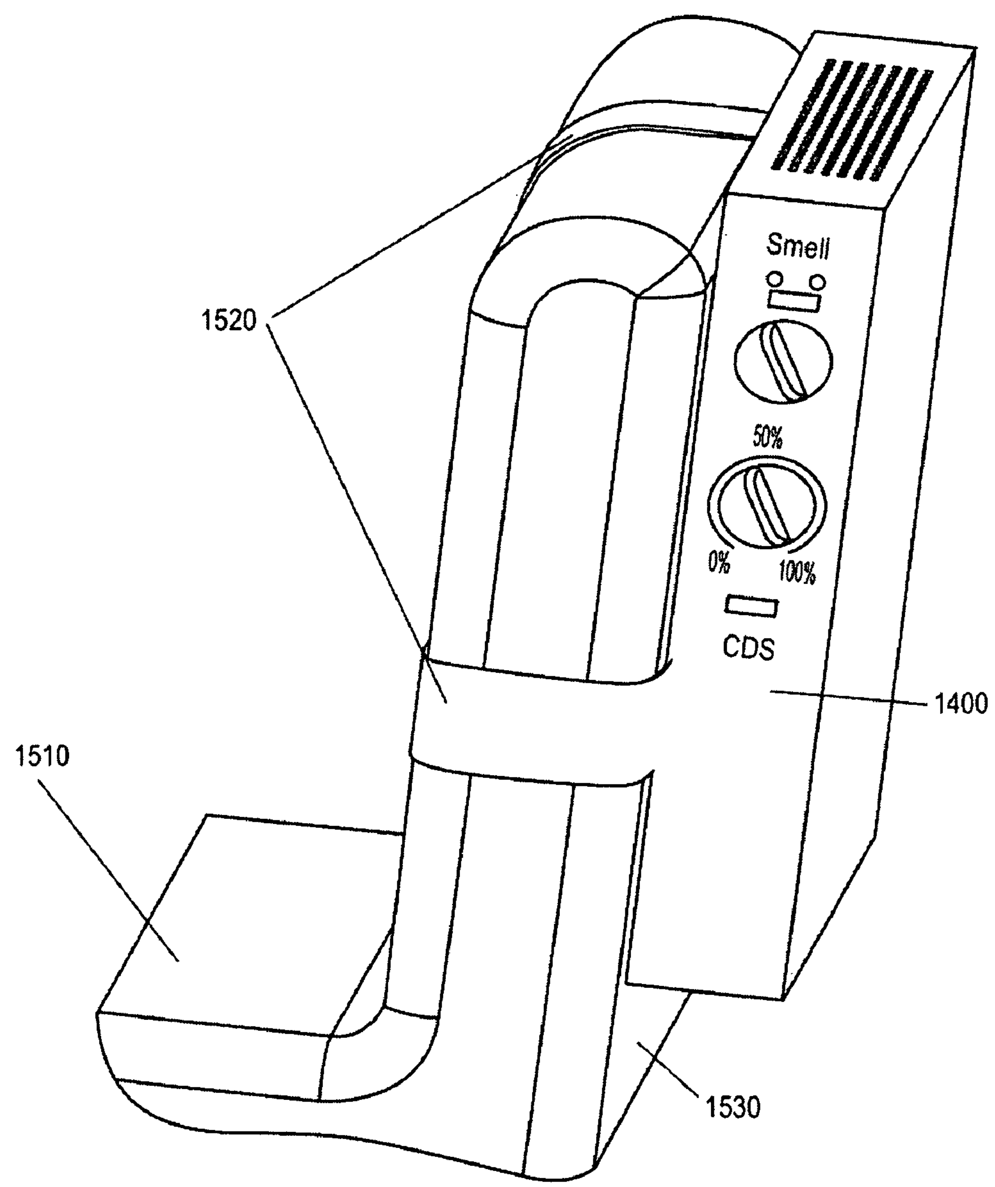
FIG. 15 illustrates the portable system 1400 being attached to an automobile seat in accordance with one embodiment.

FIG. 15 illustrates the portable system 1400 being attached to an automobile seat in accordance with one embodiment. Belts 1510 and 1520 attach or fasten the portable system to a back 1530 of an automobile seat 1510. The portable system 1400 can attach to various other objects. Alternatively, the portable system 1400 may include no belts and not be attached to other objects.

In some embodiments, the portable system 1400 can be implemented in various facilities, including homes, commercial buildings, movie theaters, spas, hotels, etc. The portable system 1400 can be a stand-alone system or be attached to a wall, a door, a piece of furniture, etc.

The operations of exemplary methods described in the present invention can be performed in a different order, sequence, and/or have more or less operations than described. For example, in certain embodiments, an intensity of a previously selected fragrance is adjusted prior to a new fragrance being selected.

In the following description, numerous details are set forth. It will be apparent, however, to one skilled in the art, that the present invention may be practiced without these specific details. In some instances, well-known structures and devices are shown in block diagram form, rather than in detail, in order to avoid obscuring the present invention. It is to be understood that the above description is intended to be illustrative, and not restrictive. Many other embodiments will be apparent to those of skill in the art upon reading and understanding the above description. The scope of the invention should, therefore, be determined with reference to the appended claims, along with the full scope of equivalents to which such claims are entitled.

What is claimed is:

1. An air fragrance system for use in a vehicle, comprising:

an air fragrance block having a plurality of cartridges for storing a plurality of fragrances, the plurality of cartridges each having a float and a supervising valve, wherein the float location within each cartridge is indicative of an amount of fragrance stored in each cartridge, and wherein the supervising valve becomes engaged to prevent access to at least one of the plurality of cartridges when the float within the at least one of the plurality of cartridges reaches a predetermined minimum level; and a control unit coupled to the air fragrance block, to control a selection of one fragrance to be distributed within an interior of the vehicle.

2. The system of claim 1, wherein the control unit to control an intensity of the selected fragrance to be distributed within the interior of the vehicle.

3. The system of claim 2, wherein the control unit further comprises a user interface for controlling the selection and the intensity of the fragrance to be distributed within the interior of the vehicle.

4. The system of claim 1, wherein the fragrance is distributed from the air fragrance block to the interior of the vehicle via an air circulating system of the vehicle.

5. The system of claim 1, wherein the air fragrance block further comprises an isolation mechanism to isolate one or more fragrances which are not selected and the isolation mechanism to prevent these one or more fragrances from evaporating when not being selected by the control unit.

6. The system of claim 5, wherein the air fragrance block further comprises one or more electromagnetic valves associated with each cartridge;

an air intake coupled to a compressor, the compressor to force air through an inlet air line and through open electromagnetic valves associated with a selected cartridge; and a final air line to send the air fragrance received from the selected cartridge to the air circulating system for distribution within the vehicle.

7. The system of claim 1, wherein the air fragrance block is located in an engine compartment of the vehicle.

8. A portable multi-air fragrance system, comprising:

an air fragrance block having a plurality of cartridges for storing a plurality of fragrances, the plurality of cartridges each having a float and a supervising valve, wherein the float location within each cartridge is indicative of an amount of fragrance stored in each cartridge, and wherein the supervising valve becomes engaged to prevent access to at least one of the plurality of cartridges when the float within the at least one of the plurality of cartridges reaches a predetermined minimum level; and a control unit coupled to the air fragrance block, to control a selection of one fragrance to be distributed from the portable multi-air fragrance system.

9. The system of claim 8, wherein the control unit to control an intensity of the fragrance to be distributed from the portable multi-air fragrance system.

10. The system of claim 9, wherein the control unit further comprises a user interface for controlling the selection and the intensity of the fragrance to be distributed from the portable multi-air fragrance system.

11. The system of claim 8, further comprising an air fragrance diffuser to distribute the fragrance from the portable multi-air fragrance system.

12. The system of claim 8, wherein the air fragrance block further comprises an isolation mechanism to isolate one or more fragrances which are not selected and the isolation mechanism to prevent these one or more fragrance from evaporating when not being selected by the control unit.

13. The system of claim 12, wherein the air fragrance block further comprises one or more electromagnetic valves associated with each cartridge;

an air intake coupled to a compressor, the compressor to force air through an inlet air line and through open valves electromagnetic associated with a selected cartridge; and a final air line to send the air fragrance received from the selected cartridge to the air circulating system for distribution within the vehicle.

14. The system of claim 8, wherein the system is located in an interior of a vehicle.

15. A method of providing multiple air fragrances, comprising:

providing an air fragrance block having a plurality of cartridges to store a plurality of fragrances, the plurality of cartridges each having a float and a supervising valve, wherein the float location within each cartridge is indicative of an amount of fragrance stored in each cartridge;

detecting the float location and, responsive to detecting that the float location has reached a predetermined minimum level in at least one of the plurality of cartridges, engaging the supervising valve to prevent access to the at least one of the plurality of cartridges; and controlling a selection of one fragrance to be distributed within an interior of a vehicle with a control unit.

16. The method of claim 15, further comprising:

controlling an intensity of the selected fragrance to be distributed within the interior of the vehicle with the control unit.

17. The method of claim 16, wherein controlling the selection of one fragrance further comprises selecting one fragrance with a disk of management in which a managing contact couples to a contact associated with a cartridge causing an inlet valve and a final valve to open airways to and from the selected cartridge.

18. The method of claim 17, further comprising:

controlling a selection and an intensity of a different fragrance to be distributed within the interior of the vehicle with the control unit.

19. The method of claim 15, further comprising:

distributing one or more fragrances from the air fragrance block to the interior of the vehicle via an air circulating system of the vehicle.

20. The method of claim 16, further comprising:

isolating one or more fragrances which are not selected; and preventing these one or more fragrances from evaporating when not being selected by the control unit.

* * * * *